(12) United States Patent
Zobel et al.

(10) Patent No.: US 9,151,877 B1
(45) Date of Patent: Oct. 6, 2015

(54) DEFLECTIVE OBJECTIVE FOR FLEXIBLE AND SEMI-FLEXIBLE ENDOSCOPES

(75) Inventors: Jurgen Zobel, Pembroke Pines, FL (US); Zoltan A. Bodor, Plantation, FL (US); Peter P. Bodor, Pembroke Pines, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 867 days.

(21) Appl. No.: 13/428,714

(22) Filed: Mar. 23, 2012

Related U.S. Application Data

(60) Provisional application No. 61/467,628, filed on Mar. 25, 2011.

(51) Int. Cl.
*G02B 3/00* (2006.01)
*A61B 1/005* (2006.01)
*A61B 1/00* (2006.01)

(52) U.S. Cl.
CPC .............. *G02B 3/00* (2013.01); *A61B 1/00163* (2013.01)

(58) Field of Classification Search
CPC ...... G02B 3/00; G02B 23/24; G02B 23/2407; G02B 23/2415; G02B 23/2423; G02B 23/2446; A61B 1/00163; A61B 1/307
USPC .......... 351/431, 433, 720, 737–740; 600/101, 600/127, 129, 130, 160–177; 359/431, 433, 359/720, 737–740
See application file for complete search history.

(56) References Cited

U.S. PATENT DOCUMENTS

| | | | | |
|---|---|---|---|---|
| 4,138,192 A | * | 2/1979 | Yamasita | 359/726 |
| 4,655,557 A | * | 4/1987 | Takahashi | 359/735 |
| 5,980,453 A | * | 11/1999 | Forkey et al. | 600/162 |

* cited by examiner

*Primary Examiner* — Darryl J Collins
(74) *Attorney, Agent, or Firm* — C. Brandon Browning; Maynard Cooper Gale

(57) ABSTRACT

An objective assembly for use with small endoscopes like uretheroscopes, the objective assembly including a lens having an optical surface that includes a partial wedge. The partial wedge directly faces an aperture stop thereby limiting the F-number of the objective.

17 Claims, 3 Drawing Sheets

DEFLECTIVE OBJECTIVE FOR FLEXIBLE AND SEMI-FLEXIBLE ENDOSCOPES

RELATED APPLICATIONS

This application claims priority to U.S. provisional patent application Ser. No. 61/467,628, filed on Mar. 25, 2011, and titled, DEFLECTIVE OBJECTIVE FOR FLEXIBLE AND SEMI-FLEXIBLE ENDOSCOPES, the entire contents of which are incorporated herein by reference.

FIELD OF THE INVENTION

The present invention is directed to an objective assembly for use with endoscopes, and more particularly, to an deflective objective assembly including a partial wedge lens for minimizing an air gap between the partial wedge and an opposed optical component.

BACKGROUND OF THE INVENTION

Small flexible or semi-flexible endoscopes, like a uretheroscopes, uretero-renoscopes or other small flexible and semi-flexible instruments, have an outer diameter that ranges from 1 mm to 3 mm. Within the small area defined by the cross-section of such scopes there are illumination bundles for illuminating an object to be inspected, an imaging system for transmitting an image of the illuminated object to the physician, channels through which instrumentation and fluid irrigation can pass and an outer tube containing all these components. As a result, space within the outer tube is limited. In many instances, the diameter available within the outer tube for the imaging system is less or much less than a millimeter (mm).

Image bundles, which together with an objective form part of the imaging system, receive an image from the objective and transmit the image to an eyepiece or video chip for display to a physician. The outer diameter of the image bundles range from 0.16 mm to 0.85 mm. Based upon diffraction limits, these image bundles have pixels in the range of 1,600 to 30,000 with pixel sizes of not less than 5 μm to 61 μm. Compared to large instruments, these image bundles exhibit a low resolution, and therefore, the optical quality required of the objective for creating the distal image on the image bundle are also low.

Even though the optical quality required of the objective in systems utilizing image bundles having diameters ranging from 0.16 mm to 0.85 mm is low, it remains difficult to manufacture objectives for small scopes in a traditional manner. Lenses are traditionally made from glass lens blanks glued on a metal pin. The first optical surface of the lens is ground and polished. The lens is then removed and glued on a second pin where the second surface is ground and polished in the same way. Using this traditional method, objectives having a lens of 1 mm or more can be made.

To make lenses having a diameter of less than 1 mm, for example, as required in very small endoscopes, manufacturers start with glass balls in the sub-millimeter range. Balls of mineral glass or optical glass can be manufactured in large quantities in the sub millimeter range. Precision of the diameter of these glass balls are within optical tolerances, and the polished surfaces have optical quality. A large amount of these glass balls can be glued together on a tool and plano surfaces can be ground on one side of the balls. This remaining ball having a plano surface can be glued on a small pin and a cylinder surface can be ground on the periphery. This is a proven method for creating a simple plan convex lens in the sub millimeter range.

FIG. 1 depicts a conventional objective using two plano convex lenses 10, 12 made out of glass balls. The first lens 10 is an objective lens where the plano surface faces an object side 14 and is fixed in the head of a endoscope. The second lens 12 is a field lens facing an image bundle and is cemented on the image bundle (not shown). The image bundle with field lens 12 can be moved relative to objective lens 10 to adjust the focus of the objective system comprised by objective lens 10 and field lens 12. Light entering the objective is not limited, but the acceptance angle of the fibers in the image bundle has a limited numerical aperture which limits the f-number of the objective system.

For endoscopes used with instruments that are guided in an instrument channel of the endoscopes, the optical systems of the endoscopes are laterally displaced to the instrument channel. To have the instruments visible in the instrument channel as early as possible, optical systems often include a deflection component at the tip of the optical system. For example, referring to FIG. 2, some optical systems have a wedged surface 16 on a distal side on a front lens 18. In this case, the deflection angle depends highly on the optical parameters of the medium in which the endoscope is used. Often endoscopes are used in a liquid medium contained within a body cavity. However, the objective assembly is not immersed in the liquid so the deflection during viewing does not accurately represent the real application.

Referring to FIG. 3, there is depicted an objective with a wedge 20 facing the inside of the objective system. In this case, the deflection changes much less because the main deflection happens on the inside of the objective assembly where the distal medium has no influence. However, if the outside surface 21 of the lens is perpendicular, the optical axis is still slightly deflected when the distal medium changes. A corrected deflection in depicted in FIG. 4 where a surface 22 facing the distal medium is angled so that the surface is perpendicular to the optical axis of a wedge surface 24. However, the technical difficulties with his arrangement are high compared to the advantages. Accordingly, the preferred angulation for smaller optical systems in endoscopes is as represented in FIG. 3.

The limitation of the brightness through the amount of light accepted by the imaging fibers has disadvantages. Any light entering the objective system but not accepted by the imaging fibers results in glare and reflections. Aperture stops used to avoid the entrance of light in the optical system which is not used in the imaging system. A prior art method of applying an aperture is to deposit a non-transparent coating on a glass plate with a circular opening in the middle. Such aperture stops can be produced in very high accuracy and quantity on one glass plate. The individual apertures are then separated and ground down to the right diameter. A preferred application is an aperture stop on a glass plate cemented on the plano side of a plano convex objective lens where the aperture stop faces the plano surface of the lens.

A current deflective objective assembly including a wedge 26 and an objective 28 with an aperture stop 30 is depicted in FIG. 5. The integrated aperture stop 30 allows for reduction of the effective diameter of objective lens 28 compared to the diameter of the image bundle and field lens 32 to which the objective is coupled. As a result, wedge 26 and objective lens 28 with aperture stop 30 can have a smaller diameter than field lens 32. As displayed in FIG. 6, since wedge 26 and objective 28 have a smaller diameter, they can be contained within a small sleeve 34 having an outer diameter that is that is equal to the outer diameter of the image bundle and field leans 32. Sleeve 34, containing wedge 26 and objective 28, can then be glued as a unit within the distal objective head of an endoscope. A shortcoming of this combination is that its very difficult to assemble in the objective head.

The fact that these subassemblies of wedge and objective lens are in the range of a few tenth of a millimeters poses the risk that the small subassemblies, when glued in the distal tips of endoscopes, will not always be perfectly sealed. To improve the quality of such seals, it is known to glue a front window made from mineral glass or resistant hard optical glass to the object side of the subassemblies. Such subassemblies are shown in FIGS. 7 and 8. FIG. 7 depicts a configuration where a front window 31 is glued to a sleeve 34 containing a wedge 36 and an objective lens 38 with an aperture stop 40. Sleeve 34 is extended in the direction of the image side so that it can act as a guide for a field lens 42. In this arrangement, wedge 36 and objective 38 each have an outer diameter that is the same as the outer diameter of field lens 42. FIG. 8 illustrates a similar configuration but with a shorter sleeve 44 and a larger diameter field lens 46. In this arrangement, sleeve 44 can be glued in the distal tip of the endoscope, and field 46 lens can be moved freely with the image bundle relative to the objective for focusing an image onto field lens 48.

Each of the objective assembly designs described above include shortcomings that make the assembly of them difficult and their rate of failure relatively high. This is especially true for objective assemblies having a large field of view where the ray heights increase with the distance to the aperture stop. Thus, even with axial thicknesses of a few tenths or less, the accumulation of optical components within the assembly can result in relative large ray heights at the front surface and the field lens. Also through asymmetric deflection, ray heights on one side of the front window do not increase proportionally resulting in glare, reflections or cut-off of the image.

SUMMARY OF THE INVENTION

The present invention is directed to an objective assembly for use with very small flexible and semi-flexible endoscopes such as uretheroscopes and uretero-renoscopes. The objective assembly maintains the advantages of reasonable manufacturability and assembly combined with a high image quality without glare, reflections and image cut-off. The advantages of the objective assembly are achieved by minimizing the distance between an effective wedge and an aperture stop. The wedge is only partially applied to the surface of an opposing glass plate to minimize the air gap or distance between the wedge and the opposed optical component. Additionally the aperture stop is in direct opposition to the partial wedged surface. This aperture stop can be on the plano surface of the wedge or on the plano surface of the front window glued to the partial wedge or on a glass plate where the aperture stop is facing directly the wedge. Alternatively, the partial wedge can be applied to the plane surface of the objective lens facing the front window which has the aperture stop on that surface facing the partial wedge on the objective lens. If the aperture stop is between the objective side and the wedge, the aperture stop can be de-centered to improve symmetric ray trace in the field lens.

According to one aspect of the invention, there is provided an objective assembly includes a first lens, a second lens, an aperture stop positioned between the first lens and the second lens and an air gap located between the first lens and the second lens. The first lens includes a first optical surface and an opposing second optical surface, the first optical surface including a third optical surface defining a first plane and a fourth optical surface defining a second plane that intersects the first plane. The first lens and aperture stop are arranged so that the third optical surface is in contact with the aperture stop and the air gap is located between the fourth optical surface and the second lens. The entirety of the third optical surface is in contact with the aperture stop such that no air gap exists between the third optical surface and the second lens. The aperture stop is applied to a plano surface of the second lens.

According to another aspect of the invention, there is provided an objective assembly includes a first lens having a first optical surface and an opposing second optical surface, the first optical surface including a third optical surface defining a first plane and a fourth optical surface defining a second plane that intersects the first plane. A second lens is located on an object side of the first lens, and a third lens is located an image side of the first lens. Positioned between the first lens and the second lens is an aperture stop wherein the opposing second optical surface is in contact with the aperture stop and the third optical surface is in contact with the third lens. An air gap is located between the fourth optical surface of the first lens and the third lens which does not does not extend between the third optical surface and the third lens.

According to yet another aspect of the invention, there is provided an endoscope having an objective assembly that includes a first lens having a first optical surface and an opposing second optical surface, the first optical surface including a plano surface and an angled surface relative to the plano surface. A second lens is pressed against the plano surface of the first lens, and an air gap is located between the angled surface and the second lens. An aperture stop is located between the first lens and the second lens with the aperture stop being pressed against the second optical surface of the first lens.

DETAILED DESCRIPTION OF PRESENTLY PREFERRED EMBODIMENTS

The present invention is directed to an objective assembly for use with small endoscopes. The objective assembly includes a lens having an optical surface that is provided as a partial wedge. The partial wedge is composed of at least two distinct surfaces. A first surface is arranged to press flatly against a plano surface of an opposing lens with no gap being formed there between. A second surface extends from its intersection with the first surface, away from the opposing lens, such that an air gap is formed between the second surface and the opposing lens. By including the partial wedge, the length of the air gap along the axis of the objective assembly is shorter than if the optical surface of the lens included a single flat or wedged surface that contacted the opposing lens only at an outer edge of the wedge surface. To limit the focal ratio of the objective assembly, an aperture stop is supported on a plano surface of the opposing lens directly across from the partial wedge or on a plano surface of the lens or another lens located on an image side of the objective assembly. FIGS. 9 through 13 illustrate various embodiments of the invention.

Figure 1:
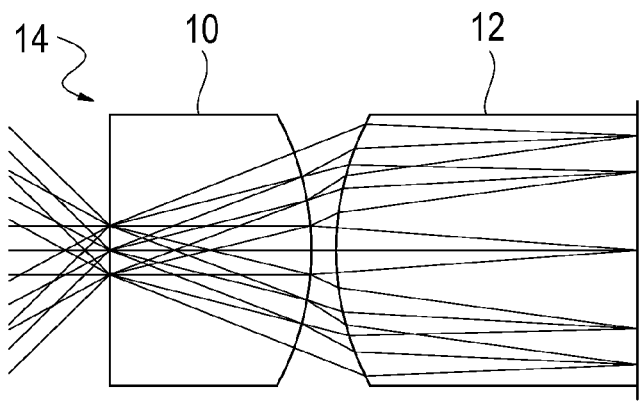
FIG. 1 is a sectional view of a first prior art objective assembly.
Figure 2:
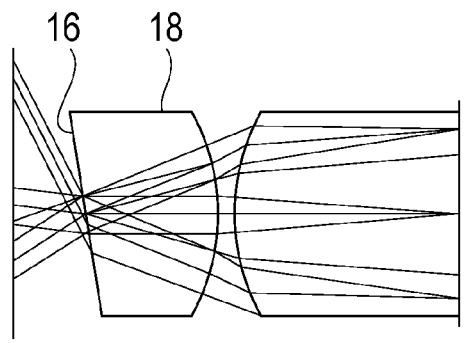
FIG. 2 is a sectional view of a second prior art objective assembly.
Figure 3:
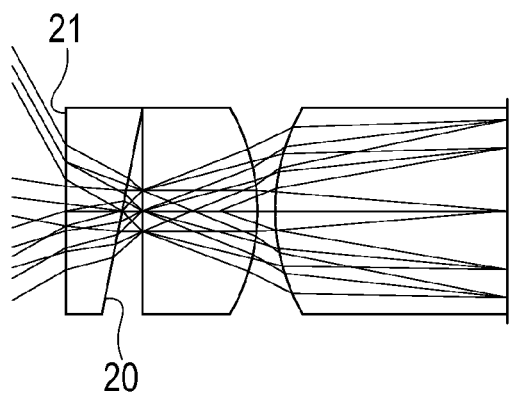
FIG. 3 is a sectional view of a third prior art objective assembly.
Figure 4:
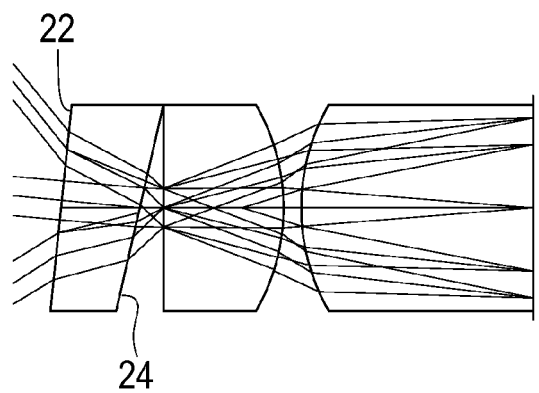
FIG. 4 is a sectional view of a fourth prior art objective assembly.
Figure 5:
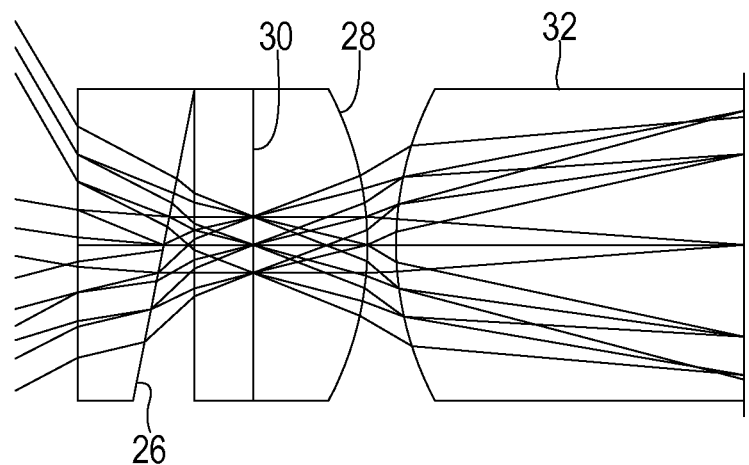
FIG. 5 is a sectional view of a fifth prior art objective assembly.
Figure 6:
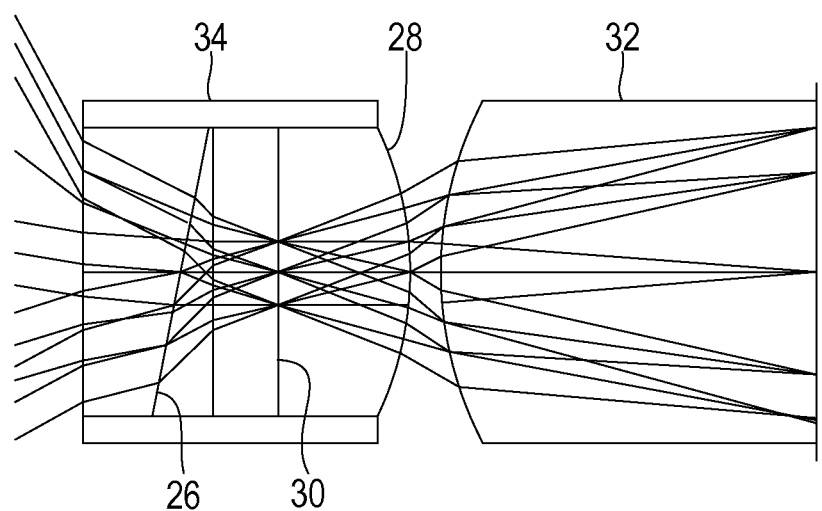
FIG. 6 is a sectional view of the fifth prior art objective assembly including a sleeve.
Figure 7:
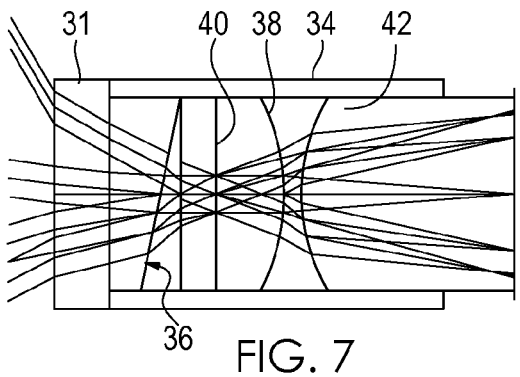
FIG. 7 is a sectional view of a sixth prior art objective assembly.
Figure 8:
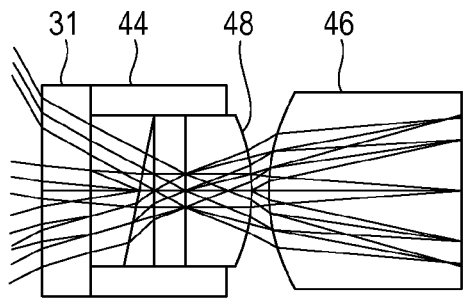
FIG. 8 is a sectional view of a seventh prior art objective assembly.
Figure 9:
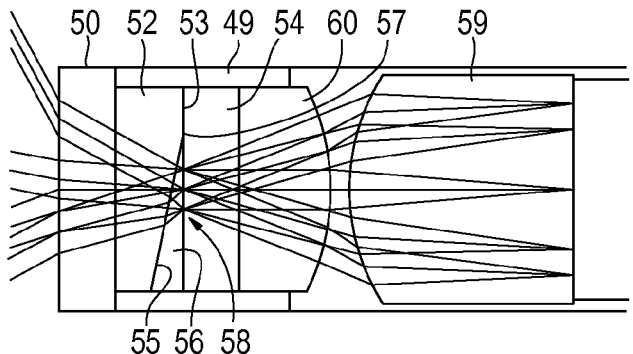
FIG. 9 is sectional view of an objective assembly according to a first embodiment of the present invention.

Referring to FIG. 9, there is depicted an objective assembly contained within a sleeve 49. A plano-plano glass plate 50 seals the object-side of sleeve 49 and is glued to plano surface of an object-side of a partial wedge lens 52. Partial wedge lens 52 includes a first optical surface 53 that is pressed against a plano-plano glass plate 54 and a second optical surface 55 that is integral with first optical surface 53. First optical surface 53 defines a first plane that intersects at point 57 with a second plane defined by second optical surface 55. Second optical surface 55 extends away from glass plate 54 thereby creating an air gap 56 between partial wedge 52 and glass plate 54. An aperture stop 58 is centrally located on the object-side of glass plate 54. Glass plate 54 is glued to a plano surface of a plano convex objective lens 60. Aperture stop 58 is oriented to face partial wedge lens 52 rather than objective lens 60. In this way, the relative distance between second optical surface 55 of partial wedge lens 52, across air gap 56, and aperture stop 58 is minimized. Objective lens 60 is aligned with a field lens 59 having an outer diameter than is greater than the outer diameter of objective lens 60 and partial wedge lens 55.

Figure 10:
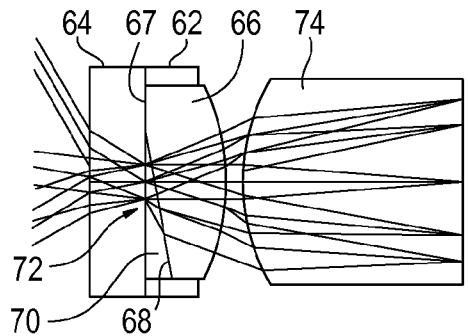
FIG. 10 is sectional view of an objective assembly according to a second embodiment of the present invention.

Referring to FIG. 10, there is depicted an objective assembly contained within a short sleeve 62. The objective assembly contained within sleeve contains a plano-plano glass plate 64 which seals the object-side of sleeve 62 and a partial wedge lens 66 that is glued to an image side of glass plate 64. In particular, partial wedge lens 66 is an objective lens that includes a first optical surface 67 that is pressed against glass plate 64 and a second optical surface 68 that is integral with first optical surface 67. Second optical surface 68 extends away from glass plate 64 thereby creating an air gap 70 between partial wedge lens 66 and glass plate 64. An aperture stop 72 is centrally located on the image-side of glass plate 64. Aperture stop 72 is oriented to face second surface 68 of partial wedge lens 52. In this way, the relative distance between second optical surface 68 of partial wedge lens 66, across air gap 70, and aperture stop 72 is minimized. Partial wedge lens 66 is aligned with a field lens 74 having an outer diameter than is greater than the outer diameter of partial wedge lens 66. The embodiment depicted in FIG. 10 is suggested where the field of view is large and the relative ray heights increase dramatically. That is because this embodiment relies upon a single glass plate and eliminates the requirement of two glass plates, as described for the objective assembly depicted in FIG. 9.

Figure 11:
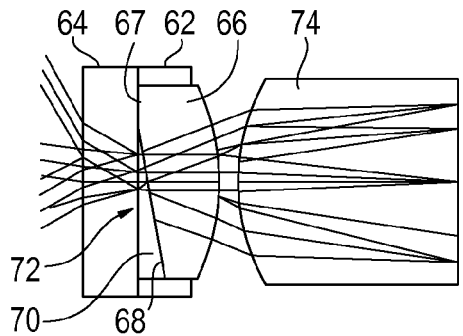
FIG. 11 is sectional view of an alternative arrangement for the objective assembly of FIG. 10.

Referring to FIG. 11, there is depicted an alternatively arranged objective assembly to the objective assembly of FIG. 10, where like portions share like numbering. The objective assembly depicted in FIG. 11 is identical to the objective assembly depicted in FIG. 10 with the exception of the placement of aperture stop 72 on glass plate 64. In particular, aperture 72 of the objective assembly depicted in FIG. 10, is centered on the image side of glass plate 64. As a result, a asymmetric ray trace is formed in field lens 74 and partial wedge lens 66. In the objective assembly depicted in FIG. 11, this is avoided by placing aperture stop 72 slightly off-center on glass plate 64 relative to the optical axis of lenses 64, 66 and 74, as well as an image bundle (not shown) affiliated with field lens 74.

Figure 12:
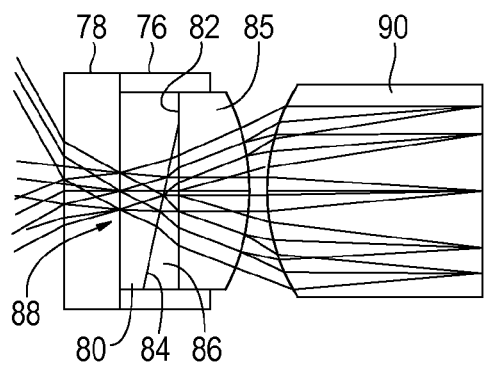
FIG. 12 is sectional view of an objective assembly according to a third embodiment of the present invention.

Referring to FIG. 12, there is depicted an objective assembly contained within a short sleeve 76. A plano-plano glass plate 78 seals the object-side of sleeve 76 and is glued to plano surface of an object-side of a partial wedge lens 80. Partial wedge lens 80 includes a first optical surface 82 that is pressed against a plano surface of plano convex objective lens and a second optical surface 84 that is integral with first optical surface 82. Second optical surface 84 extends away from objective lens 85 thereby creating an air gap 86 between second surface 84 of partial wedge lens 80 and objective lens 85. An aperture stop 88 is centrally located between glass plate 78 and partial wedge lens 80. Aperture stop 88 can be supported in the image side of glass plate 78 or the object side of partial wedge lens 80. Objective lens 85 is aligned with a field lens 90 having an outer diameter than is greater than the outer diameter of objective lens 85 and partial wedge lens 80. As with the objective assemblies depicted in FIGS. 10 and 11, by eliminating the need of a separate glass plate for supporting the aperture stop, this embodiment is suggested for use with objectives having a large field of view.

Figure 13:
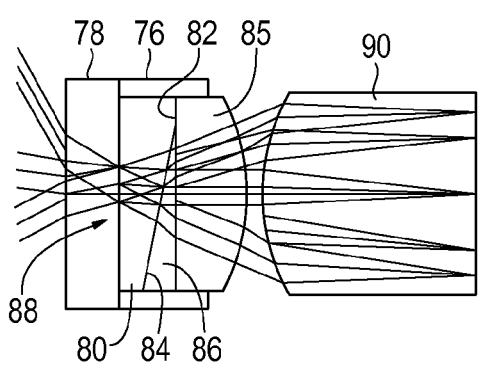
FIG. 13 is sectional view of an alternative arrangement for the objective assembly of FIG. 12.

Referring to FIG. 13, there is depicted an alternatively arranged objective assembly to the objective assembly of FIG. 12, where like portions share like numbering. The objective assembly depicted in FIG. 13 is identical to the objective assembly depicted in FIG. 12 with the exception of the placement of aperture stop 80 between glass plate 78 and partial wedge lens 80. In particular, aperture 88 of the objective assembly depicted in FIG. 12, is centered on the image side of glass plate 78. As a result, a asymmetric ray trace is formed in field lens 90 and objective lens 85. In the objective assembly depicted in FIG. 13, this is avoided by placing aperture stop 88 slightly off-center between glass plate 78 and partial wedge 80 relative to the optical axis of lenses 78, 76, 85 and 90, as well as an image bundle (not shown) affiliated with field lens 90.

The field lenses for all the different embodiments described above are glued on the respective image bundle and can freely move with the image bundle to adjust the focus of the combined objective system.

As will be apparent to one skilled in the art, various modifications can be made within the scope of the aforesaid description. Such modifications being within the ability of one skilled in the art form a part of the present invention and are embraced by the claims below.

It is claimed:

1. An objective assembly comprising:
    a first lens having a first optical surface and an opposing second optical surface, the first optical surface including a third optical surface defining a first plane and a fourth optical surface defining a second plane that intersects the first plane,
    a second lens,
    an aperture stop positioned between the first lens and the second lens, and
    an air gap located between the first lens and the second lens,
    wherein the third optical surface is in contact with the aperture stop and no air gap exists between the third optical surface and the second lens.

2. The objective assembly according to claim 1 wherein the air gap is located between the fourth optical surface and the second lens.

3. The objective assembly according to claim 1 wherein the entirety of the third optical surface is in contact with the aperture stop.

4. The objective assembly according to claim 1 wherein the aperture stop is applied to a plano surface of the second lens.

5. The objective assembly according to claim 1 further comprising, in order from an object side to an image side of the assembly, a plano-plano glass plate, the first lens, the aperture stop, the second lens, and a plano objective lens.

6. The objective assembly according to claim 1 further comprising, in order from an object side to an image side of the assembly, the second lens, the aperture stop and the first lens, wherein the first lens is a plano objective lens and the first optical surface is located on a plano side of the plano objective lens.

7. The objective assembly according to claim 1 wherein the objective assembly is contained in an endoscope.

8. The objective assembly according to claim 1 further comprising a flexible image bundle optically aligned with the first lens and the second lens.

9. An objective assembly comprising:
   in order from an object side to an image side of the assembly, a second lens, an aperture stop and a first lens, a first lens having a first optical surface and an opposing second optical surface, the first optical surface including a third optical surface defining a first plane and a fourth optical surface defining a second plane that intersects the first plane, wherein the aperture stop is positioned between the first lens and the second lens, and
   an air gap located between the first lens and the second lens, wherein the third optical surface is in contact with the aperture stop and the first lens is a plano objective lens and the first optical surface is located on a plano side of the plano objective lens.

10. The objective assembly according to claim 9 wherein the air gap is located between the fourth optical surface and the second lens.

11. The objective assembly according to claim 9 wherein no air gap exists between the third optical surface and the second lens.

12. The objective assembly according to claim 9 wherein the entirety of the third optical surface is in contact with the aperture stop.

13. The objective assembly according to claim 9 wherein the aperture stop is applied to a plano surface of the second lens.

14. The objective assembly according to claim 9 further comprising, in order from an object side to an image side of the assembly, a plano-plano glass plate, the first lens, the aperture stop, the second lens, and a plano objective lens.

15. The objective assembly according to claim 9 wherein the objective assembly is contained in an endoscope.

16. The objective assembly according to claim 9 further comprising a flexible image bundle optically aligned with the first lens and the second lens.

17. The objective according to claim 9 wherein the aperture stop is not centered on a surface on which it is supported.

\* \* \* \* \*